United States Patent
Gebhardt et al.

(10) Patent No.: US 10,118,882 B2
(45) Date of Patent: Nov. 6, 2018

(54) PROCESS FOR THE PREPARATION OF SUBSTITUTED PHENYL KETONES

(71) Applicant: BASF Agro B.V., Arnhem (NL)

(72) Inventors: Joachim Gebhardt, Ludwigshafen (DE); Daniel Saelinger, Ludwigshafen (DE); Manfred Ehresmann, Maxdorf (DE); Roland Goetz, Neulussheim (DE)

(73) Assignee: BASF AGRO B.V., Arnhem (NL)

( * ) Notice: Subject to any disclaimer, the term of this patent is extended or adjusted under 35 U.S.C. 154(b) by 0 days.

(21) Appl. No.: 15/736,974

(22) PCT Filed: Jun. 14, 2016

(86) PCT No.: PCT/EP2016/063647
§ 371 (c)(1),
(2) Date: Dec. 15, 2017

(87) PCT Pub. No.: WO2016/202807
PCT Pub. Date: Dec. 22, 2016

(65) Prior Publication Data
US 2018/0170848 A1   Jun. 21, 2018

(30) Foreign Application Priority Data
Jun. 17, 2015   (EP) .................................... 15172535

(51) Int. Cl.
| | | |
|---|---|---|
| *C07C 45/00* | (2006.01) | |
| *C07D 249/08* | (2006.01) | |
| *C07D 301/00* | (2006.01) | |
| *C07C 45/64* | (2006.01) | |
| *C07D 301/02* | (2006.01) | |
| *C07C 49/80* | (2006.01) | |
| *C07C 49/84* | (2006.01) | |

(52) U.S. Cl.
CPC ............ *C07C 45/004* (2013.01); *C07C 45/64* (2013.01); *C07C 49/80* (2013.01); *C07C 49/84* (2013.01); *C07D 249/08* (2013.01); *C07D 301/02* (2013.01)

(58) Field of Classification Search
CPC .................................................... C07C 45/004
See application file for complete search history.

(56) References Cited

FOREIGN PATENT DOCUMENTS

| | | |
|---|---|---|
| WO | WO 2013007767 | 1/2013 |
| WO | WO 2014108286 | 7/2014 |
| WO | WO 2015091045 | 6/2015 |
| WO | WO 2016005211 | 1/2016 |

OTHER PUBLICATIONS

International Search Report dated Aug. 10, 2016, prepared in International Application No. PCT/EP2016/063647.
International Preliminary Report on Patentability dated Dec. 7, 2017, prepared in International Application No. PCT/EP2016/063647.

*Primary Examiner* — Sikarl A Witherspoon
(74) *Attorney, Agent, or Firm* — Brinks Gilson & Lione

(57) ABSTRACT

The present invention relates to a process for providing substituted phenyl ketones. Furthermore, the invention relates to the use of substituted phenoxyphenyl ketones obtained by the inventive process for the preparation of triazoles.

12 Claims, No Drawings

PROCESS FOR THE PREPARATION OF SUBSTITUTED PHENYL KETONES

This application is a National Stage application of International Application No. PCT/EP2016/063647, filed Jun. 14, 2016. This application also claims priority under 35 U.S.C. § 119 to European Patent Application No. 15172535.5, filed Jun. 17, 2015.

The present invention relates to a process for providing substituted phenyl ketones.

Furthermore, the invention relates to the use of substituted phenoxyphenyl ketones obtained by the inventive process for the preparation of triazoles.

The substituted phenyl ketones provided by the process according to the present invention are valuable intermediate compounds for the synthesis of triazole compounds having pesticidal, in particular fungicidal activity. WO 2013/007767 is directed to fungicidal substituted 1-[4-phenoxy-2-(halogenalkyl)phenyl]-2-(1,2,4-triazol-1-yl)ethanol compounds, that can be synthesized via a respective phenyl ketone intermediate compound. WO 2014/108286 (EP 13150663.6; PCT/EP2013/077083), WO 2015/091045 (PCT/EP2014/076839) and WO2016/005211 (EP14176130.4; PCT/EP2015/064550) describe improved process steps and processes in the synthesis of certain fungicidally active triazole compounds.

The methods known from the literature are sometimes not suitable for the efficient synthesis of substituted phenyl ketones because the yield or purity is not sufficient and/or the reaction conditions and parameters such as temperature are not optimal because they lead to unwanted side products and/or less yields. Because said substituted phenyl ketones are valuable intermediates for the synthesis of triazole compounds with promising fungicidally activity, there is an ongoing need for improved processes that easily make such intermediates and compounds available.

An object of the present invention was to provide an improved process for the synthesis of substituted phenyl ketones (II) that are valuable intermediates for the preparation of fungicidally active triazole compounds circumventing the disadvantages of the known processes.

In particular, it has now been found that lowering the temperature during the reaction to compounds (II) from compounds (III) surprisingly reduces the unwanted side products dramatically and, at the same time, the reaction times remain such that the process is industrially valuable.

The present invention relates thus to a process for the preparation of the ketone compounds

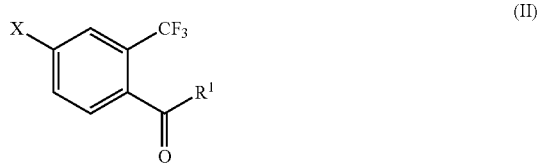

(II)

wherein
X is F or Cl and
$R^1$ is $C_1$-$C_6$-alkyl or $C_3$-$C_8$-cycloalkyl;
comprising the following step:
(i) reacting a compound of the formula (III)

(III)

with R'—Mg-Hal (IV) or Mg, and $R^1$C(=O)Cl (V), wherein the temperature during the reaction with (V) is kept in the range of −20° C. to 10° C., wherein
R' is $C_1$-$C_4$-alkyl or $C_3$-$C_6$-cycloalkyl and
Hal is halogen.

In the process step (i) according to the present invention, substituted phenyl compounds of formula (III), wherein X is F or Cl, are used.

The 2-bromo-5-fluoro/chloro-benzotrifluoride of the formula (III) is reacted with the Grignard reagent R'—Mg-Hal (IV) or magnesium (Mg).

According to a preferred embodiment, the Grignard reagent R'—Mg-Hal (IV) is used in the process. R' in the Grignard reagent is $C_1$-$C_4$-alkyl or $C_3$-$C_6$-cycloalkyl, in particular it is selected from methyl, ethyl, isopropyl, tert-butyl, sec-butyl and cyclopropyl. Specifically, R' in the Grignard reagent is selected from isopropyl, tert-butyl, sec-butyl and cyclopropyl. In one specific embodiment, R' is isopropyl. In one further embodiment, R' is sec-butyl. Hal stands for halogen, in particular Cl or Br. Also more than one Grignard reagent can be used in the same reaction, such as, for example reagent (IV), wherein Hal is Br together with the respective reagent (having the same R'), wherein Hal is Cl. According to one embodiment, Hal is Cl and R' in the Grignard reagent is selected from isopropyl, tert-butyl, sec-butyl and cyclopropyl. According to a further embodiment, Hal is Br and R' in the Grignard reagent is selected from isopropyl, tert-butyl, sec-butyl and cyclopropyl. In one preferred embodiment, in the inventive process, the Grignard reagent is (iso-propyl)-Mg—Cl and/or (iso-propyl)-Mg—Br, in particular (iso-propyl)-Mg—Cl or (iso-propyl)-Mg—Br. In a further embodiment, the Grignard reagent contains both, (iso-propyl)-Mg—Cl and (iso-propyl)-Mg—Br. In one further preferred embodiment, in the inventive process, the Grignard reagent is (sec-butyl)-Mg—Cl and/or (sec-butyl)-Mg—Br, in particular (sec-butyl)-Mg—Cl or (sec-butyl)-Mg—Br. In a further embodiment, the Grignard reagent contains both, (sec-butyl)-Mg—Cl and (sec-butyl)-Mg—Br.

Preferably, the Grignard reagent is used in an amount of 1 eq to 2 eq, in particular 1.1 to 1.8 eq, more specifically 1.2 to 1.6 eq, in relation to one equivalent of compound (III). In particular, the amounts of 1.3 to 1.5 eq, more particularly 1.2 to 1.4 eq per mole of compound (III) may be favorable according to the present invention. It may be also favorable, if the amounts are 1 to 1.3 eq, more particularly 1.1 to 1.2 eq per mole of compound (III). It can also be preferred if the amounts are 1.15 to 1.45 eq, in particular 1.15 to 1.35 eq per mole of compound (III). Usually, the Grignard reagent is used in excess, preferably in slight excess.

One further embodiment relates to the inventive process, wherein Mg is used then forming a Grignard reagent with compound (III) and then reacting with compound (V). It can be preferred if Mg is used in an amount slightly less than compound (III). Here, the same details regarding solvents apply.

As generally known to the skilled person, the structure of a Grignard reagent can be described by the so-called Schlenck equilibrium. A Grignard reagent undergoes a solvent-dependent equilibrium between different magnesium compounds. The Schlenck equilibrium for the Grignard reagent used according to the present invention can be schematically illustrated as follows:

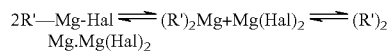

Furthermore, it is known that solvent molecules, in particular ethers such as diethylether or THF, which are commonly used for reactions with Grignard reagents, can add to the magnesium of the Grignard reagent thereby forming etherates.

Depending on the solvent used in the inventive reaction, solvent molecules may add to the Mg-reagents, thereby forming—in case of the use of ethers—the respective etherates. For general information regarding structures of Grignard reagents, see also Milton Orchin, Journal of Chemical Education, Volume 66, Number 7, 1999, pp 586 to 588.

According to an embodiment of the inventive process, LiCl is added to the reaction mixture of step (i). According to an alternative, before contacting the Grignard reagent (IV) with the reagents of the inventive process, it is brought together with LiCl, thereby forming an addition product R'MgHal.LiCl((IV).LiCl). According to this alternative, ((IV).LiCl) is then used in step (i). The use of LiCl together with Grignard reagents is generally known in the art, see for example Angew. Chem. Int. Ed. 2004, 43, 3333 and Angew. Chem. Int. Ed. 2006, 45, 159.

The Grignard reagents (IV) or their addition products with LiCl ((IV).LiCl) are commercially available or can be made according to processes well-known to the skilled person (see Angew. Chem. Int. Ed. 2004, 43, 3333).

In the carbonyl chloride (acid chloride) $R^1C(=O)Cl$ (V), as well as in the other compounds having this variable, such as (II), (IA), (IB) and (IC), $R^1$ is $C_1$-$C_6$-alkyl or $C_3$-$C_8$-cycloalkyl, in particular selected from $CH_3$, $CH(CH_3)_2$ and cyclopropyl.

According to one embodiment, $R^1$ is $C_1$-$C_6$-alkyl, more specifically $C_1$-$C_4$-alkyl, in particular selected from $CH_3$, $C_2H_5$, n-$C_3H_7$, $CH(CH_3)_2$, n-butyl, iso-butyl and tert-butyl, more particularly selected from $CH_3$, $C_2H_5$, $CH(CH_3)_2$ and $C(CH_3)_3$, even more particularly $CH_3$ or $CH(CH_3)_2$. In one particularly preferred embodiment, $R^1$ is $CH_3$. According to a further embodiment, $R^1$ is $C_3$-$C_8$-cycloalkyl, in particular $C_3$-$C_6$-cycloalkyl, such as $C_3H_5$ (cyclopropyl), $C_4H_7$ (cyclobutyl), cyclopentyl or cyclohexyl. A further embodiment relates to compounds, wherein $R^1$ is $C_3H_5$ (cyclopropyl) or $C_4H_7$ (cyclobutyl), more specifically cyclopropyl.

The carbonyl chloride (acid chloride) $R^1C(=O)Cl$ (V) is preferably used in an equimolar amount or in excess compared to the reagent of formula (III). Specifically, the carbonyl chloride (acid chloride) is used in an amount of 1 eq to 3 eq, in particular 1.1 to 2.5 eq, more specifically 1.2 to 2 eq, in relation to one equivalent of compound (III). In particular the amounts of 1.3 to 1.8 eq, more specifically 1.4 to 1.6 eq per mole of compound (III) may be favorable according to the present invention. Usually, the carbonyl chloride (acid chloride) is used in excess, preferably in slight excess.

The Grignard reagent is added in the manner as is common to the skilled person. In particular, it can be added as solution in an appropriate solvent such as tetrahydrofurane (THF), 1,4-dioxane, diethylether and 2-methyl-tetrahydrofurane.

Examples for appropriate solvents for step (i) of the inventive process are aprotic organic solvents such as for example diethylether, tetrahydrofurane (THF), methyl-tert-butylether (MTBE), toluene, ortho-xylene, meta-xylene, para-xylene and mixtures thereof. Typically, the Grignard reagent is added as solution in THF, 1,4-dioxane, diethylether or 2-methyl-tetrahydrofurane (2-Me-THF), in particular in THF or diethylether, to the reaction vessel or flask containing the reagent (III) and a solvent such as, for example, toluene, MTBE, ortho-xylene, meta-xylene, para-xylene, mesitylene and/or diisopropylether, in particular toluene, MTBE and/or ortho-xylene.

The temperature for the reaction of the Grignard reagent in step (i) may be from −20° C. to 70° C. and is preferably held at a maximum of 50° C., in particular at a maximum of 40° C., more preferably at a maximum of 35° C. Generally, it is preferred to have a reaction temperature of 20° C. to 45° C., in particular room temperature to 45° C., in particular 25° C. to 40° C. In a further embodiment, the temperature is 20° C. to 35° C., specifically 25° C. to 30° C.

Within the framework of the present invention, it has been found that the optimal temperature range during the reaction with reagent $R^1C(=O)Cl$ (V) is −20° C. to 10° C. In particular, according to a specific embodiment of the present invention, the temperature is held at −15° C. to 5° C., more specifically at −10° C. to −5° C.

It may be preferred, if a Cu(I)-catalyst is added in step (i). In particular, the Cu(I) catalyst may preferably be present for the reaction with reagent (V). An appropriate Cu(I)-catalyst for the inventive process is a Cu(I) salt or Cu(I) oxide, in particular a Cu(I) salt such as Cu(I)Cl or Cu(I)Br or any mixture thereof. According to one specific embodiment, Cu(I)Cl is used.

Thus, according to one embodiment, the 2-bromo-5-fluoro/chloro-benzotrifluoride of the formula (III) is reacted with the Grignard reagent R'—Mg-Hal (IV) or magnesium (Mg) and the acyl chloride $R^1C(=O)Cl$ (V) in the presence of a Cu(I) catalyst in an amount of 0.005 to 0.065 mol equivalents per 1 mol of compound (III). See also WO 2015/091045 (PCT/EP2014/076839).

It may be preferred if 0.005 to 0.055 mol equivalents per 1 mole of compound (III) are used. In particular, the Cu(I)-catalyst is added in an amount of 0.005 to 0.045 mol equivalents per 1 mole of compound (III). Also, it may be preferred if 0.055 to 0.045 mol equivalents per 1 mole of compound (III), more specifically 0.005 to 0.04 mol equivalents per 1 mole of compound (III) are used. In particular, the amount of Cu(I)-catalyst is 0.01 to 0.03 mole equivalents per 1 mole of compound III, more particularly 0.015 to 0.025 mole equivalents, even more particularly 0.015 to 0.02, per 1 mole of compound III, specifically 0.018 to 0.023 mole equivalents per 1 mole of compound (III). According to one embodiment, the Cu(I)-catalyst is added in several portions to the reaction mixture, for example in two portions a half of the total amount.

An appropriate course of reaction is such that the Grignard reagent is first reacted with the compound of formula (III) and then, this reaction mixture is added to the carbonyl chloride (acid chloride) and a portion of the Cu(I)-catalyst, in particular half of the total amount of the Cu(I) catalyst. After about half of the Grignard mixture has been added to the carbonyl chloride (acid chloride) reaction mixture, the remaining amount of Cu(I) is added. According to a further embodiment, the whole amount of Cu(I)-catalyst is added in one portion.

According to still a further preferred embodiment, the Cu(I)-catalyst and part of the acid chloride (such as 0.5% to 10%, more specifically 2% to 6%, in particular up to 5%) and the solvent are added first and then, the remaining acid chloride and the Grignard mixture (prepared from the Grignard reagent and the compound of formula (III)) are added concurrently.

According to a further embodiment, the acid chloride is added gradually to the Cu(I)-catalyst and the reaction mixture of Grignard reagent and the compound of formula (III).

After step (i), a work-up of the reaction mixture can be carried out by procedures known in a general manner to the person skilled in the art. For example, after completion of the reaction, water is added. Sometimes it is practicable to add the reaction mixture to water after completion of the reaction followed by the respective further work up. Instead of water, aqueous acidic solutions can be used and either be added to the reaction mixture or the other way around, wherein it is preferred if the reaction mixture is added to the acidic solution.

Thereafter, the organic phases are washed with water and the solvent is removed from the separated organic phases.

Further, it may be appropriate to wash the organic phases with acidic or basic aqueous solution instead or in addition to washing with water.

The so-obtained raw product can be directly used in the next process step, i.e. step (ii) of the inventive process. However, the raw product can also be further worked up and/or purified as generally known to the skilled person. If this is deemed appropriate, the reaction mixture is extracted with a suitable organic solvent (for example aromatic hydrocarbons such as toluene and xylenes) and the residue is, if appropriate, purified by recrystallization and/or chromatography. By means of the inventive process, unwanted side-products, such as cleavage products resulting from the solvent(s) used and/or secondary products derived therefrom, can be avoided. For example, if THF is used as solvent such unwanted side-products may occur. The kind of side products that are observed further depend on the Mg compound (IV) and the acylation reagent (V) used. Consequently, a major advantage of the inventive process is, that less side products occur that might disturb the following synthesis steps. Overall, by means of the inventive process, the selectivity of the reaction is increased. At the same time, however, also the reaction time remains appropriate. In particular, it is avoided according to the inventive process, that high amounts of one and the same side product are formed. It is generally unfavorable if a relatively high percentage of one particular unwanted side product is formed. The separation is difficult and, as a result, the side products may lead to further unwanted secondary products in following process steps. When carrying out the inventive process step (i) it is possible that each side product is present in an amount of not more than 5% (5% or less), in particular equal to or less than 2%.

According to a further embodiment of the invention, in step (i) no $AlCl_3$ is added to the reaction. Consequently, the reaction is carried out in the absence of or at least essentially without $AlCl_3$. In particular, at most traces of $AlCl_3$ are present, such as at most 0.0065 mol % $AlCl_3$, for example traces due to impurities of other reagents.

The starting compounds (III) for the inventive process can be synthesized as known to the skilled person, in analogy to similar known syntheses or they are also partly commercially available. See in particular WO 2013/007767 and the citations therein. In WO 2014/108286 favorable process details are outlined. See also JACS 1965, 87, p 1353ff, Heterocycles 8, 1977, p. 397 ff, Synth. Communications, 15, 1985, p 753, J. Agric. Food Chem. 2009, 57, 4854-4860 and DE3733755.

The inventive process leads to compounds (II) that are valuable intermediates for the synthesis of fungicidal triazole compounds. In the following, a possible synthesis route to such fungicides using said intermediates (II) is described:

Consequently, the present invention also relates to a process for the preparation of triazole compounds of the formula (IC)

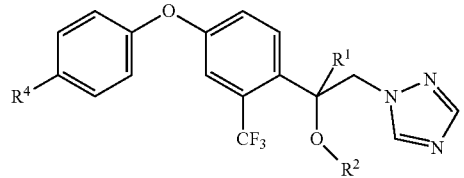

wherein $R^1$ is defined and preferably defined herein or as in any one of claims 1 to 7 and $R^2$ is hydrogen, $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkyl-$C_1$-$C_6$-alkyl, phenyl, phenyl-$C_1$-$C_4$-alkyl, phenyl-$C_2$-$C_4$-alkenyl or phenyl-$C_2$-$C_4$-alkynyl;

wherein the aliphatic moieties of $R^2$ are not further substituted or do carry one, two, three or up to the maximum possible number of identical or different groups $R^{12a}$ which independently are selected from:

$R^{12a}$ halogen, OH, CN, nitro, $C_1$-$C_4$-alkoxy, $C_3$-$C_8$-cycloalkyl, $C_3$-$C_8$-halocycloalkyl and $C_1$-$C_4$-halogenalkoxy;

wherein the cycloalkyl and/or phenyl moieties of $R^2$ are not further substituted or do carry one, two, three, four, five or up to the maximum number of identical or different groups $R^{12b}$ which independently are selected from:

$R^{12b}$ halogen, OH, CN, nitro, $C_1$-$C_4$-alkyl, $C_1$-$C_4$-alkoxy, $C_1$-$C_4$-halogenalkyl, $C_3$-$C_8$-cycloalkyl, $C_3$-$C_8$-halocycloalkyl and $C_1$-$C_4$-halogenalkoxy; and $R^4$ is F or Cl comprising the following steps:

(i) according to invention as described above and in any one of claims 1 to 9;

(ii) reacting compound (II) as defined in step (i) with a phenol derivative of formula (VI)

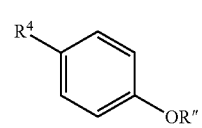

wherein

R" is hydrogen or an alkali metal kation, e.g. Li+, Na+ or K+, in particular Na+;

in the presence of a base if R" is hydrogen to result in a ketone of formula (IA)

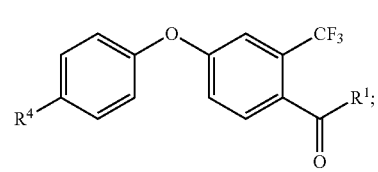

(iii) reacting the ketone of the formula (IA) as defined in step (ii) to oxiranes (IB);

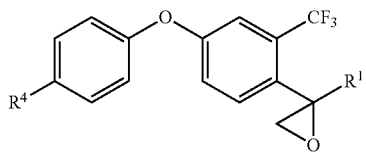

(IB)

and
(iv) reacting the oxirane (IB) as defined in step (iii) with 1H-1,2,4-triazole in the presence of a base to obtain compounds (IC), wherein $R^2$ is hydrogen (compounds IC-1); and, for obtaining compounds wherein $R^2$ is different from hydrogen (compounds IC-2):
(v) derivatizing the compound of formula (IC-1) as defined in step (iv) under basic conditions with $R^2$-LG, wherein LG is a nucleophilically replaceable leaving group; to result in compounds (IC-2).

According to step (ii), compounds (II) are reacted with a phenol of formula (VI) in the presence of a base.

R" in formula (VI) is hydrogen ((VI) is a substituted phenol) or a alkali metal kation ((VI) is a substituted phenolate). $R^4$ in formula (VI) and formulae (IA), (IB) and (IC), respectively, is F or Cl, in particular Cl.

As described above, compound (II) can be used directly from step (i) without further purification or can be used in purified form.

Examples for appropriate solvents for step (ii) of the inventive process are aprotic organic solvents such as for example dimethyl formamide (DMF), N-methyl pyrrolidone (NMP), Dimethyl imidazolidinone (DMI), toluene, o-xylene, dimethylactamide (DMA) and any mixtures thereof. In particular DMF, NMP, toluene and DMA or any mixtures, more specifically DMF, are particularly suitable.

According to one embodiment, the solvent used in step (ii) contains not more than 8 eq DMF in relation to 1 eq of the phenol of formula (VI), in particular not more than 7 eq to 1 eq of the phenol of formula (VI), more specifically not more than 6 eq to 1 eq of the phenol of formula (VI). It may be preferred if not more than 7.5, specifically not more than 6.5 eq DMF are used in the process of the invention.

It may be preferred, if the solvent used in step (ii) contains not more than 3 eq DMF in relation to 1 eq of the phenol of formula (VI), in particular not more than 2.8 eq to 1 eq of the phenol of formula (VI), more specifically not more than 2.6 eq to 1 eq of the phenol of formula (VI). It may be preferred if not more than 2.4 eq, specifically not more than 2.2 eq DMF are used in the process of the invention.

The base used in step (ii) is preferably an inorganic base, according to one embodiment selected from NaOH, KOH, $Na_2CO_3$ and $K_2CO_3$, more specifically from $Na_2CO_3$ and $K_2CO_3$. According to one particular embodiment, $Na_2CO_3$ is used. According to a further particular embodiment, $K_2CO_3$ is used.

The base can be used in solid form or as a solution, e.g. as aqueous solution.

The reagents for step (ii) are preferably added at ambient temperature and the reaction temperature is then elevated, wherein the reaction temperature after the reagents have been added is preferably held at a maximum of 150° C., in particular at a maximum of 140° C., more preferably at a maximum of 130° C. Generally, it is preferred to have a reaction temperature of 20° C. to 135° C., in particular 50° C. to 135° C., more particularly 100° C. to 130° C. For example, when using 4-chlorophenol as phenol derivative of formula (VI) it can be favorable if (VI) is handled as solution in a solvent such as DMF.

According to a further embodiment, the phenol derivative of formula (VI) (such as 4-chlorophenol) is added as melt, wherein the reaction temperature is then raised as detailed above after the reagents have been added.

After step (ii), a work-up of the reaction mixture can be carried out by procedures known in a general manner to the person skilled in the art. Generally, water is added and the aqueous phase is extracted with a suitable solvent, e.g. toluene or o-xylene. The raw product obtained after evaporation of the solvent(s) can directly be used in a further step, if desired. However, the raw product can also be further worked up and/or purified as generally known to the skilled person.

According to one embodiment, after completion of the reaction, most of the solvent (e.g. DMF or toluene) is removed from the reaction mixture, preferably under reduced pressure. Then, a suitable organic solvent, such as, for example, toluene or o-xylene, is added together with water. According to the inventive process, it may be favorable to carry out one to three, preferably two extractions of the aqueous phase.

In process step (iii), for obtaining an oxirane from the keto group, compound (IA) is preferably reacted with a trimethylsulf(ox)onium halide $((CH_3)_3S^+ (O)Hal^-)$ (VII) or trimethylsulfonium methylsulfate of the formula (VIII) $(CH_3)_3S^+ CH_3SO_4^-$.

According to one embodiment, in the process step (iii), the ketone (IA) is reacted with trimethylsulfonium methylsulfate of the formula VIII $(CH_3)_3S^+ CH_3SO_4^-$, preferably in aqueous solution in the presence of a base.

Step (iii) for the preparation of oxiranes (IB) particularly is as follows:
(iii) reacting an oxo compound of the formula (IA) with trimethylsulfonium methylsulfate of the formula VIII $(CH_3)_3S^+CH_3SO_4^-$          VIII in aqueous solution in the presence of a base, wherein the variables $R^1$, $R^4$ are defined as given and preferably described herein for compounds (IA).

In this process step (iii) using trimethylsulfonium methylsulfate of the formula VIII, preferably, 1 to 4 equivalents, in particular 1.2 to 3.5 eq, more specifically 1.5 to 3.3 eq, of water in relation to one equivalent of compound (IA) are used. It may be favorable, if more than 1.5 eq of water, in particular more than 1.5 eq of water to 4 eq of water, more specifically more than 1.5 eq to 3.5 eq of water, even more particularly more than 1.5 eq water to 2.5 eq water per mole of compound (IA) are used. In particular the ratios of 1.6 to 3.8, more specifically 1.7 to 3.3 eq, more specifically 1.8 to 2.8 eq or 1.9 to 2.5 of water per mole of compound (IA) may be favorable according to the present invention. According to a further embodiment, more than 1.5 eq of water, in particular more than 2 eq of water, more specifically more than 2.5 eq of water per mole of compound (IA) are used. In particular, 1.6 to 5, more specifically 1.7 to 4 eq, more specifically 1.8 to 3.5 eq of water per mole of compound (IA) may be favorable according to the present invention.

The reagent VIII is preferably used in an amount of 1.1 to 2.5, in particular 1.2 to 2, more specifically 1.3 to 1.6 equivalents of VIII per 1 equivalent (mole) of compound (IA).

In general, the reagent of formula VIII can be prepared from dimethylsulfide and dimethylsulfate. According to one embodiment, reagent VIII is prepared in-situ by adding dimethylsulfate to the reaction mixture containing dimethylsulfide. According to a further embodiment, either dimethylsulfide or dimethylsulfate is charged first and the other reagent is then added, wherein it may be preferred to add dimethylsulfide to a reaction mixture containing dimethylsulfate. The dimethylsulfide is usually used in excess. In particular, dimethylsulfide is generally used in amounts so that the reagent VIII is sufficiently formed during the reaction. The molar ratio between dimethylsulfide and dimethylsulfate for the formation of the reagent VIII is 1:1 to 2:1. Preferably, the molar ratio between dimethylsulfide and dimethylsulfate is 1:1 to 1.5:1, more preferably 1:1 to 1.4:1. It may be also preferred to use 1 to 1.3, in particular 1 to 1.25, more specifically 1 to 1.1 eq dimethylsulfide in relation to one equivalent of dimethylsulfate.

It is preferred to use as reagent VIII an aqueous solution of trimethylsulfonium methylsulfate containing 33 to 37 wt %, preferably 34 to 36 wt %, more specifically 34 to 35.3 wt %, also more specifically 34.3 to 35.9 wt %, of trimethylsulfonium kation.

In particular, the reagent VIII solution contains 33 to 37 wt %, preferably 34 to 36 wt %, more specifically 34 to 35.3 wt %, also more specifically 34.3 to 35.9 wt %, of trimethylsulfonium kation. Accordingly, the amount of trimethylsulfonium-methylsulfate in the reagent, measured as summation of trimethsulfonium-cation and methylsulfate-anion, is about 80 to 90 wt %, preferably about 83 to 88 wt-%, more specifically about 83 to 86 wt-%. The quantification can be, for example, accomplished by means of quantitative NMR-spectroscopie.

The viscosity of the aqueous reagent VIII solution is comparatively low. The solutions are stable at room temperature, in particular at 25° C., and can be stored over a longer time. In particular, the reagent solution does not crystallize out during storage over a longer time, such as several weeks, e.g. up to 12 weeks, at temperatures of 10 to 25° C.

The reagent can be prepared by adding dimethylsulfate to water and dimethylsulfide. Dimethylsulfide is normally used in excess, generally 2 to 8, more preferably 4 to 6, more specifically 4.5 to 5.5, equivalents.

In the preparation of the aqueous solution of reagent VIII, in particular 0.8 to 2.2 eq, more preferably 0.9 to 1.2 eq, water in relation to the dimethylsulfate are used. It may also be preferred if in the preparation of the aqueous solution of reagent VIII, preferably 1.3 to 2.2 eq, more preferably 1.45 to 2.0 eq, water in relation to the dimethylsulfate are used.

Preferably, the temperature of the reaction mixture when adding the dimethylsulfate is room temperature, in particular 25° C. to 40° C.

The aqueous reagent separates as the lower phase and can be further used as such.

The use of the aqueous solution of the reagent VIII has been proven very efficient also for up-scaled reaction conditions, since it is stable and since it contains a defined amount of reagent, so that reagent VIII can be easily and precisely dosed to the reaction mixture.

Thus it is a preferred embodiment, if the reagent VIII is added as an aqueous solution of trimethylsulfonium methylsulfate containing 33 to 37 wt %, preferably 34 to 36 wt %, more specifically 34 to 35.3 wt %, also more specifically 34.3 to 35.9 wt % of trimethylsulfonium kation.

According to one embodiment of the inventive process, dimethylsulfide is also used as solvent in step (iii). According to a further embodiment, an additional solvent is used. In particular, an aprotic organic solvent is suitable, such as for example diethylether, methyl-tert-butylether, chlorobenzene, xylene or toluene.

The base that can be used in step (iii) is preferably selected from KOH and NaOH. In a preferred embodiment, KOH is used, preferably as solid pellets or flakes. It is preferred if at least 3 equivalents of base, preferably at least 3.2 eq, more specifically at least 3.4 eq per 1 equivalent of compound (IA) are used. It may be preferred if the amount of base is 3 to 6 eq, more specifically 3 to 5 eq per mole of compound (IA).

The reaction temperature when adding KOH in step (iii) is preferably held at a maximum of 60° C., more specifically at a maximum of 50° C. Generally, it is also preferred to have a reaction temperature when adding KOH of at least 20° C., in particular at least room temperature, in particular at least 25° C. In a further embodiment, the temperature is at least 30° C. It may be preferred if the temperature is at least 35° C. or at least 45° C. The temperature of the reaction mixture can for example be held in these ranges by adding the KOH in portions.

The overall reaction temperature in step (iii) is preferably held at a maximum of 70° C., in particular at a maximum of 60° C., more preferably at a maximum of 50° C. Generally, it is also preferred to have a reaction temperature of at least 20° C., in particular at least room temperature, in particular at least 25° C. In a further embodiment, the temperature is at least 30° C. It may be preferred if the temperature is at least 35° C.

In case a work-up of the reaction mixture after step (iii) is suitable, it can be carried out by procedures known in a general manner to the person skilled in the art. It may be preferred if water is added to the reaction mixture after completion of step (iii) and the resulting mixture is heated while stirring dependent on the melting point of the organic content. The temperature during this heating is held preferably from 30° C. to 70° C., more specifically 40° C. to 60° C., even more specifically 50° C. to 60° C. The organic phase may, for example, be separated and dissolved in a suitable solvent such as dimethyl formamide (DMF), N-methylpyrrolidone (NMP), dimethylsulfoxide (DMSO) or dimethylacetamide (DMAC). Dimethylsulfide, if still present, is preferably removed by distillation before or after the solvent addition. The reaction mixture may then be used directly for the next step or, if appropriate, further worked-up and/or purified by e.g. recrystallization and/or chromatography.

According to one further specific embodiment, in step (iii), the oxo compound of the formula (IA) is reacted with dimethyl sulfide $(CH_3)_2S$ and dimethylsulfate $(CH_3)_2SO_4$, forming the reagent VIII, trimethylsulfonium methylsulfate $[(CH_3)_3S^+ CH_3SO_4^-]$, in aqueous solution in the presence of potassium hydroxide (KOH), wherein dimethyl sulfide and dimethyl sulfate are used in a molar ratio of 1:1 to 2:1, and wherein at most 10 weight-% organic solvent in relation to the amount of compound (IA), are added. For details see also WO2016/005211 (PCT/EP2015/064550; EP14176130.4). In this embodiment, the reagent of formula VIII is formed from dimethylsulfide and dimethylsulfate. In particular, reagent VIII is prepared in-situ. Either dimethylsulfide or dimethylsulfate is charged first and the other reagent is then added. It may be preferred to add dimethylsulfide to a reaction mixture containing dimethylsulfate.

The dimethylsulfide and dimethylsulfate are preferably used in such amounts that the reagent VIII is present in the reaction mixture in an amount of 1.1 to 2.5, in particular 1.2 to 2, more specifically 1.3 to 1.6 equivalents of VIII per 1 equivalent (mole) of compound (IA).

Dimethylsulfide is used in amounts so that the reagent VIII is sufficiently formed during the reaction. The molar ratio between dimethylsulfide and dimethylsulfate for the formation of the reagent VIII is 1:1 to 2:1. Preferably, the molar ratio between dimethylsulfide and dimethylsulfate is 1:1 to 1.5:1, more preferably 1:1 to 1.4:1. It may be also preferred to use 1 to 1.3, in particular 1 to 1.25, more specifically 1 to 1.1 dimethylsulfide in relation to one equivalent of dimethylsulfate.

This reaction step can be carried out with at most 10 weight-% of organic solvents in relation to the amount of compound (IA) [amount of solvent: (amount of solvent+ amount of compound III)]. In particular, the reaction can be carried out using at most 8 weight-%, more specifically at most 5 weight-%, even more specifically at most 3 weight-%, of organic solvents in relation to the amount of compound (IA). More specifically, in the reaction mixture, at most 2 weight-%, more specifically at most 1 weight-% of organic solvents in relation to the amount of compound (IA) are added.

In a specific embodiment, in this step (iii) essentially no organic solvent is added. In particular, in step (iii) no organic solvent is added apart from the reagents used.

Organic solvents are liquid organic compounds that dilute the reactants without taking part in the reaction or catalyzing the reaction. The skilled person in the field of organic synthesis is familiar with "organic solvents" and it is clear to such skilled person what kind of solvents are "organic solvents". Examples for organic solvents are e.g. alcohols, nitrils and aromatic hydrocarbons. Alcohols are for example methanol, ethanol, propanol and butanol (e.g. tert-butanol). Aromatic hydrocarbons are for example toluene or xylenes. An example for nitrile is acetonitrile.

Reaction step (iii) is preferably carried out in aqueous solution. Preferably, water is used in an amount of 0.5 to 4 eq, in particular 0.9 to 4, in relation to one equivalent of compound (IA). According to one embodiment, relatively low amounts of water, for example 0.5 to 0.95 eq, more specifically 0.6 to 0.94, even more specifically 0.7 to 0.93 eq in relation to one equivalent of compound (IA), are used. It may also be advantageous to use 0.8 to 0.92 eq, more specifically 0.85 to 0.91, even more specifically 0.85 to 0.9 eq in relation to one equivalent of compound (IA) in the inventive process. According to a further embodiment, 0.9 to 4 equivalents, more specifically 1 to 4, in particular 1.2 to 3.5 eq, more specifically 1.5 to 3.3 eq, of water in relation to one equivalent of compound (IA) are used. It may be favorable, if more than 1.5 eq of water, in particular more than 1.5 eq of water to 4 eq of water, more specifically more than 1.5 eq to 3.5 eq of water, even more particularly more than 1.5 eq water to 2.5 eq water per mole of compound (IA). In particular the ratios of 1.6 to 3.8, more specifically 1.7 to 3.3 eq, more specifically 1.8 to 2.8 eq or 1.9 to 2.5 of water per mole of compound (IA) may be favorable according to the present invention. In one further particular embodiment, advantages can be achieved if the amounts of water used in step (iii) are 0.5 to 0.95 eq or more than 1.5 eq of water to 4 eq per mole of compound (IA).

In step (iii), preferably KOH is used. It is preferred if at least 2 equivalents of base, more specifically at least 2.5 equivalents of base, even more specifically at least 3 equivalents of base per 1 equivalent of compound (IA) are used. It may be preferably if at least 3.2 more specifically at least 3.4 eq per 1 equivalent of compound (IA) are used. Furthermore, it may be advantageous, if the amount of base is 2 to 6 eq, in particular 2.5 to 5.5 eq, more specifically 2.5 to 5 eq, even more specifically 3 to 5 eq per mole of compound (IA).

KOH is in particular used in solid form, preferably as solid pellets, flakes, micropills and/or powder.

The base, in particular solid KOH, is in particular used such that the preferred range of water present in the reaction is kept. Then, some of the base is dissolved in the reaction solution and some is still present in solid form during the reaction.

The KOH can be added in one or more portions, for example 2 to 8 portions, to the reaction mixture. KOH can also be added in a continuous manner. Preferably, the KOH is added after compound (IA) has been charged to the reaction vessel. However, the order may also be changed and the compound (IA) is added to the reaction mixture already containing the KOH.

The order of adding the reactants to the reaction mixture is variable. In one embodiment, the base is added to the solution of compound (IA) and solvent first and then reagent VIII is added. According to another embodiment, the reagent VIII is added first to the solution of compound (IA) and then the base is added. According to a further embodiment, a solution of compound (IA) and the reagent VIII are added simultaneously to the base. In the latter embodiment, the base is preferably suspended in sufficient solvent and is stirred during the addition of the reagents.

The oxiranes (IB) can be further reacted to a triazole of formula (IC) as defined above.

LG represents a nucleophilically replaceable leaving group such as halogen, alkylsulfonyl, alkylsulfonyloxy and arylsulfonyloxy, preferably chloro, bromo or iodo, particularly preferably bromo.

According to one embodiment, $R^2$ is selected from $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkyl-$C_1$-$C_4$-alkyl, phenyl, phenyl-$C_1$-$C_4$-alkyl, phenyl-$C_2$-$C_4$-alkenyl and phenyl-$C_2$-$C_4$-alkynyl, wherein the $R^2$ are in each case unsubstituted or are substituted by $R^{12a}$ and/or $R^{12b}$ as defined and preferably defined herein.

According to a further embodiment, $R^2$ is $C_1$-$C_6$-alkyl, in particular $C_1$-$C_4$-alkyl, such as $CH_3$, $C_2H_5$, $CH(CH_3)_2$, $CH_2CH_2CH_3$, $CH_2CH_2CH_2CH_3$, $CH_2CH(CH_3)_2$. A further embodiment relates to compounds, wherein $R^2$ is $C_1$-$C_6$-alkyl, in particular $C_1$-$C_4$-alkyl, that is substituted by one, two or three or up to the maximum possible number of identical or different groups $R^{12a}$, as defined and preferably defined herein. According to still another embodiment, $R^2$ is $C_3$-$C_8$-cycloalkyl-$C_1$-$C_6$-alkyl, in particular $C_3$-$C_6$-cycloalkyl-$C_1$-$C_4$-alkyl. A further embodiment relates to compounds, wherein $R^2$ is $C_3$-$C_8$-cycloalkyl-$C_1$-$C_6$-alkyl, in particular $C_3$-$C_6$-cycloalkyl-$C_1$-$C_4$-alkyl, more particularly $C_3$-$C_6$-cycloalkyl-$C_1$-$C_2$-alkyl, that is substituted by one, two or three or up to the maximum possible number of identical or different groups $R^{12a}$ in the alkyl moiety and/or substituted by one, two, three four or five or up to the maximum possible number of identical or different groups $R^{12b}$ in the cycloalkyl moiety. $R^{12a}$ and $R^{12b}$ are in each case as defined and preferably defined herein.

According to another embodiment, $R^2$ is $C_2$-$C_6$-alkenyl, in particular $C_2$-$C_4$-alkenyl, such as $CH_2CH=CH_2$, $CH_2C(CH_3)=CH_2$ or $CH_2CH=CHCH_3$. A further embodiment relates to compounds, wherein $R^2$ is $C_2$-$C_6$-alkenyl, in particular $C_2$-$C_4$-alkenyl, that is substituted by one, two or three or up to the maximum possible number of identical or different groups $R^{12a}$ as defined and preferably defined herein. According to a specific embodiment thereof, $R^2$ is $C_2$-$C_6$-haloalkenyl, in particular $C_2$-$C_4$-haloalkenyl, such as $CH_2C(Cl)=CH_2$ and $CH_2C(H)=CHCl$. According to still another embodiment, $R^2$ is $C_2$-$C_6$-alkynyl, in particular $C_2$-$C_4$-alkynyl, such as $CH_2C\equiv CH$ or $CH_2C\equiv CCH_3$. A further embodiment relates to compounds, wherein $R^2$ is $C_2$-$C_6$-alkynyl, in particular $C_2$-$C_4$-alkynyl, that is substituted by one, two or three or up to the maximum possible number of identical or different groups $R^{12a}$, as defined and preferably defined herein.

According to still another embodiment, $R^2$ is $C_3$-$C_8$-cycloalkyl, in particular $C_3$-$C_6$-cycloalkyl, such as $C_3H_5$ (cyclopropyl), $C_4H_7$ (cyclobutyl), cyclopentyl or cyclohexyl. A further embodiment relates to compounds, wherein $R^2$ is $C_3$-$C_8$-cycloalkyl, in particular $C_3$-$C_6$-cycloalkyl, such as $C_3H_5$ (cyclopropyl) or $C_4H_7$ (cyclobutyl), that is substituted by one, two, three four or five or up to the maximum possible number of identical or different groups $R^{12b}$ as defined and preferably defined herein. In a further embodiment of the invention, $R^2$ is selected from $C_1$-$C_6$-alkyl, $C_2$-$C_6$-alkenyl and $C_2$-$C_6$-alkynyl, wherein the $R^2$ are in each case unsubstituted or are substituted by $R^{12a}$ and/or $R^{12b}$ as defined and preferably defined herein. In each case, the substituents may also have the preferred meanings for the respective substituent as defined above.

$R^{12a}$ according to the invention is preferably independently selected from F, Cl, OH, CN, $C_1$-$C_2$-alkoxy, cyclopropyl, 1-F-cyclopropyl, 1-Cl-cyclopropyl and $C_1$-$C_2$-halogenalkoxy.

$R^{12b}$ according to the invention is preferably independently selected from F, Cl, OH, CN, nitro, $CH_3$, $OCH_3$, cyclopropyl, 1-F-cyclopropyl, 1-Cl-cyclopropyl and halogenmethoxy.

In one embodiment of the invention, in the process step (iv) an inorganic base is used.

The inorganic base that may be used in step (iv) is preferably selected from NaOH, KOH, $Na_2CO_3$ and $K_2CO_3$, more specifically from NaOH and KOH. According to one embodiment, NaOH is used. According to a further embodiment, KOH is used.

According to a specific embodiment, the sodium salt of 1H-1,2,4-triazole as a base is used, wherein said sodium salt is prepared using triazole and a base preferably selected from NaOH, NaH and Na-alcoholates. See also DE 3042302.

The amount of base used in step (iv) is preferably equal to or less than 1 eq, in particular less than 1 eq, more preferably equal to or less than 0.8 eq, even more preferably equal to or less than 0.6 equivalents per 1 equivalent of compound (IB). Also preferred are amounts of base being equal to or less than 0.4 equivalents, in particular equal to or less than 0.2 equivalents, specifically equal to or less than 0.1 eq per 1 equivalent of compound (IB). Preferably, at least 0.1 eq, more preferably at least 0.2 equivalents, in particular at least 0.3, more specifically at least 0.4 eq base per 1 equivalent of compound (IB) are used.

It may be favorable, if, in the synthesis of (IC-1), less than 1 eq of base is used in relation to the compound (IB). In specific embodiments thereof, NaOH is used as a base, preferably in an amount as given above, in particular in an amount of 0.1 to 0.55 eq in relation to the oxirane of formula (IB).

In order to have preferably low reaction times, temperatures of at least 100° C., more preferably at least 110° C., in particular at least 120° C. are favorable. It is also an embodiment to reflux the reaction mixture. Preferably, the reaction temperature is not higher than 150° C., in particular not higher than 140° C. Specifically, a reaction temperature of 120° C. to 140° C. is used.

The amount of 1H-1,2,4-triazole used in step (iv) generally is at least 1 eq per mole of oxirane (IB). According to one embodiment, the 1H-1,2,4-triazole is used in excess in relation to the oxirane (IB). Preferred are more than 1 eq to 2 eq, more preferably more than 1 eq to 1.8 eq, even more preferred more than 1 eq to 1.6 eq. Mostly for economic reason, it can be preferred to use at least 1.1 eq, specifically 1.15 eq, to 1.5 eq of triazole in relation to oxirane (IB).

The solvent used in step (iv) is preferably selected from dimethylformamide, dimethylacetamide, N-metylpyrrolidone. Most preferred is dimethylformamide.

According to one preferred embodiment, the compounds (IC-1) resulting from step (iv) are crystallized from a suitable solvent such as, for example toluene, an aliphatic alcohol, acetonitrile, ethyl acetate and/or cyclohexane, in particular toluene and/or an aliphatic alcohol.

Generally, one undesired side product in the synthesis of compounds IC-1 that may occur in undesired amounts is the symmetric triazole ICs-1 that is formed together with the desired triazole of formula IC-1, leading, consequently, to lower yields of the desired product.

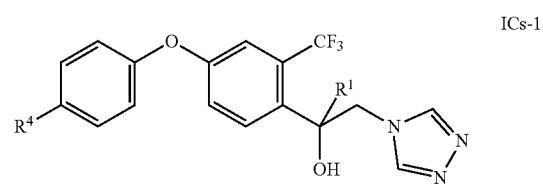

ICs-1

Consequently, according to one preferred embodiment of the invention, the products resulting from step (iv) are crystallized from a suitable solvent. This step is called final work up step (iv-1). Suitable solvents are, for example, selected from toluene, an aliphatic alcohol, acetonitrile, carbonic acid ester and cyclohexane, or any mixtures thereof, in particular from toluene, an aliphatic alcohol and carbonic acid ester and any mixture thereof.

In particular, the aliphatic alcohol is selected from methanol, ethanol, n-propanol, iso-propanol, n-butanol, isobutanol and any mixture thereof. In particular, the aliphatic alcohol is selected from methanol and ethanol and any mixture thereof.

Examples for suitable carbonic acid esters are n-butyl acetate or ethyl acetate and any mixture thereof.

Generally, for the crystallizing step, the reaction solvent, in particular dimethylformide as described above, is firstly evaporated in large part, preferably under reduced pressure.

Preferably, at least 55% of the solvent, more preferably at least 60% of the solvent, more specifically at least 70% of the solvent are removed. Specifically, it may be preferred, if at least 80%, more specifically at least 90% of the solvent, such as DMF, are removed The solvent can then be recycled to be used again in the process step (ii), if necessary after it has been further rectificated before.

Then, water and the respective suitable solvent such as an ether, for example diethylether, diisopropylether, methyl-tert-butylether (MTBE), methylenechloride and/or tolulene, in particular toluene, are added. Also ethyl acetate and/or n-butyl acetate can be appropriate as solvent. The product I is then preferably obtained by crystallization directly from the concentrated, e.g. toluene-reaction mixture. Also preferred and suitable according to the invention is the change of solvent to e.g. methanol or ethanol (see above) for the crystallization of the products.

According to one embodiment, seed crystals are added for the crystallization step.

By using the crystallizing step, in particular when carrying out the process steps (iv) the formation of the undesired symmetric triazole (ICs-1) as described above can be reduced to equal or less than 10%, more preferably equal or less than 8%, even more preferably equal or less than 5%, even more preferably equal or less than 2%.

Preferably, the ratio of isolated compound (IC-1) to the symmetric triazole (ICs-1) is at least 20:1, more preferably at least 30:1, even more preferably 50:1, more specifically 70:1. In particular, the ratio of compound (IC-1) to (ICs-1) is at least 30:1.

Also other methods of further reacting the oxiranes (IB) to end products (IC) can be carried out.

For example, the epoxide ring of compounds (IB) may be cleaved by reaction with alcohols $R^2OH$ preferably under acidic conditions to result in compounds IX:

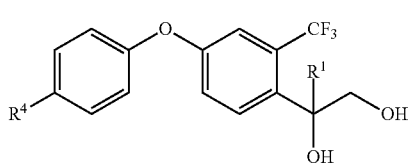

IX

Thereafter, the resulting compounds IX are reacted with halogenating agents or sulfonating agents such as $PBr_3$, $PCl_3$ mesyl chloride, tosyl chloride or thionyl chloride, to obtain compounds X wherein LG' is a nucleophilically replaceable leaving group such as halogen, alkylsulfonyl, alkylsulfonyloxy and arylsulfonyloxy, preferably chloro, bromo or iodo, particularly preferably bromo or alkylsulfonyl. Then compounds X are reacted with 1H-1,2,4-triazole to obtain compounds IC as known in the art and/or described above:

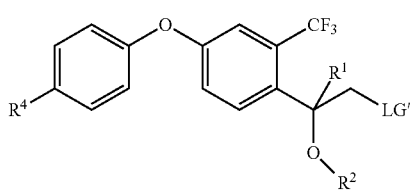

X

For obtaining compounds of formula IC, wherein the alcohol group is derivatized into an ether group to result in compounds of formula IC-2, wherein the variables are defined above, the following step can be carried out:
(v) derivatizing the compound of formula (IC-1) as defined in step (iv) under basic conditions with $R^2$-LG, wherein LG is a nucleophilically replaceable leaving group; to result in compounds (IC-2).

LG represents a nucleophilically replaceable leaving group such as halogen, alkylsulfonyl, alkylsulfonyloxy and arylsulfonyloxy, preferably chloro, bromo or iodo, particularly preferably bromo. Preferably a base is ues in step (iii) such as for example, NaH.

Suitable solvents are for example ethers, in particular cyclic ethers. Possible solvents are for example tetrahydrofuran (THF), 2-methyl-tetrahydrofuran (2-Me-THF), diethyl ether, TBME (tert-butyl methyl ether), CPME (cyclopentyl methyl ether), DME (1,2-dimethoxyethane) and 1,4-dioxane. Further solvents that may be suitable are, for example, diisopropyl ether, di-n-butyl ether and/or diglyme. Often, the use of THF or 2-methyl-THF is particularly suitable. Furthermore, it may also be suitable to use combinations of two or more different solvents, such as for example any combination of the solvents listed above or any one of the listed ethers with aliphatic hydrocarbons like n-hexane, heptane or aromatic hydrocarbons like toluene or xylenes.

The skilled person is familiar with the reaction in step (v) and may vary the reaction conditions analogously to known syntheses.

In one embodiment, a triazole compound of the formula IC is obtained by
(iv-a) reacting an oxirane of the formula (IB) as defined herein; with 1H-1,2,4-triazole and an inorganic base, wherein less than 1 equivalent of said base is used per 1 equivalent of compound (IB), resulting in compounds of formula (IC).

For obtaining compounds of formula (IC-2), wherein the alcohol group is derivatized (resulting in "$OR^2$", see above), the above derivatizing step can be carried out.

In the definitions of the variables given herein, collective terms are used which are generally representative for the substituents in question. The term "$C_n$-$C_m$" indicates the number of carbon atoms possible in each case in the substituent or substituent moiety in question.

The term "halogen" refers to fluorine, chlorine, bromine and iodine.

The term "$C_1$-$C_6$-alkyl" refers to a straight-chained or branched saturated hydrocarbon group having 1 to 6 carbon atoms, e.g. methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, 1,1-dimethylpropyl, 1,2-dimethylpropyl, hexyl, 1-methylpentyl, 2-methylpentyl, 3-methyl pentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl. Likewise, the term "$C_1$-$C_4$-alkyl" refers to a straight-chained or branched alkyl group having 1 to 4 carbon atoms, such as methyl, ethyl, propyl (n-propyl), 1-methylethyl (iso-propoyl), butyl, 1-methylpropyl (sec.-butyl), 2-methylpropyl (iso-butyl), 1,1-dimethylethyl (tert.-butyl).

The term "$C_3$-$C_8$-cycloalkyl" refers to monocyclic saturated hydrocarbon radicals having 3 to 8 carbon ring members, such as cyclopropyl, cyclobutyl, cyclopentyl, cyclohexyl, cycloheptyl or cyclooctyl. Likewise, the term "$C_3$-$C_6$-cycloalkyl" refers to monocyclic saturated hydrocarbon radicals having 3 to 6 carbon ring members, such as cyclopropyl, cyclobutyl, cyclopentyl, cyclohexyl.

The meanings and preferred meanings described herein for the variables $R^1$, $R^2$, $R^4$, X, R' and R" apply to all compounds and the precursors of the compounds and side products in any of the process steps detailed herein.

$R^4$ according to the present invention is independently selected from F and Cl. Specifically, the following compounds IC.1 to IC.7 can advantageously be prepared using the process according to the present invention:
compound IC.1 2-[4-(4-chlorophenoxy)-2-(trifluoromethyl)phenyl]-1-(1,2,4-triazol-1-yl)propan-2-ol;
compound IC.2 1-[4-(4-chlorophenoxy)-2-(trifluoromethyl)phenyl]-1-cyclopropyl-2-(1,2,4-triazol-1-yl)ethanol;
compound IC.3 2-[4-(4-chlorophenoxy)-2-(trifluoromethyl)phenyl]-3-methyl-1-(1,2,4-triazol-1-yl)butan-2-ol;
compound IC.4 2-[4-(4-chlorophenoxy)-2-(trifluoromethyl)phenyl]-1-(1,2,4-triazol-1-yl)butan-2-ol;

compound IC.5 1-[2-[4-(4-chlorophenoxy)-2-(trifluoromethyl)phenyl]-2-methoxy-propyl]-1,2,4-triazole;

compound IC.6 1-[2-[4-(4-chlorophenoxy)-2-(trifluoromethyl)phenyl]-2-cyclopropyl-2-methoxyethyl]-1,2,4-triazole;

compound IC.7 1-[2-[4-(4-chlorophenoxy)-2-(trifluoromethyl)phenyl]-2-methoxy-butyl]1,2,4-triazole;

Compounds (IC) comprise chiral centers and they are generally obtained in the form of racemates. The R- and S-enantiomers of the compounds can be separated and isolated in pure form with methods known by the skilled person, e.g. by using chiral HPLC. Furthermore, components I can be present in different crystal modifications, which may differ in biological activity. The compounds may be present in various crystal modifications. They are likewise provided by the present invention.

EXAMPLES

The following examples further illustrate the present invention and do not restrict the invention in any manner.

Examples #1 to #4

Preparation of Compound (II) with X=F, $R^1$=$CH_3$ from Compound (III), with X=F:

A mixture of isopropylchloride (32.5 g) and isopropylbromide (232 g) is added to a stirred suspension of fresh Mg turnings (55.9 g), fresh THF (1415 g) and a small holdup from the last batch (9.7 g Mg turnings and some isopropyl Grignard) at ca. 50° C. within 1 h. The resulting suspension is stirred at ca. 60° C. for another hour. After cooling to ca. 25° C., the remaining Mg turnings were allowed to settle and most of the supernatant Grignard solution (1735 g) was transferred to a solution of compound (III) (490 g) in toluene (144 g) at ca. 20-32° C. within 45 min. The resulting solution was stirred at ca. 25° C. for another hour and then transferred to a suspension of acetylchloride (196 g) and copper(I) chloride (6.1 g) in toluene (737 g) at a temperature of approximately $T_{acyl}$ (see table below) within a time of $t_{acyl}$ min. The resulting suspension was stirred at the same temperature for another hour and then hydrolyzed cautiously by the addition of fresh water and the second and third water phase of the last batch (982 g combined) at about 0° C. While the temperature was allowed to rise during workup, it was not allowed to exceed 25° C. After phase separation, the aqueous phase was discarded and the organic phase was washed with fresh water (544 g) and aq. HCl (32%, 10 g). After phase separation, the aqueous phase was kept for the next batch and the organic phase was washed with a mixture of aq. NaOH (50%, 5 g) and water (15 g). After phase separation, the aqueous phase was again kept for the next batch and the organic phase was distilled under vacuum (750-120 mbar, sump temperature up to ca. 115° C.). The resulting crude compound (II) was weighed and analyzed according to the following table 1, wherein the amount of the observed undesired side products 4-chlorobutyl acetate, 4-bromobutyl acetate and "others" (not further specified) is listed. It can be seen that working under the inventive reaction conditions leads to higher purity of the reaction product, i.e. higher content of the desired product (II):

| # | $T_{acyl}$ [° C.] | $t_{acyl}$ [min] | yield [%]$^a$ | purity [%]$^b$ | toluene [%]$^b$ | 4-chlorobutyl acetate [%]$^c$ | 4-bromobutyl acetate [%]$^c$ | others [%]$^d$ |
|---|---|---|---|---|---|---|---|---|
| 1 | 25-30 | 50 | 93.0 | 80.6 | 2.9 | 2.0 | 7.5 | 7.0 |
| 2 | 0 | 180 | 93.0 | 86.6 | 3.8 | 0.7 | 2.5 | 6.4 |
| 3 | −5 | 120 | 95.0 | 88.2 | 2.9 | 0.3 | 1.7 | 6.9 |
| 4 | −10 | 180 | 93.5 | 88.0 | 3.2 | n. d.$^e$ | 1.8 | 7.0 |

$^a$calculated from resulting weight and purity
$^b$w/w % from quantitative analytical method 1 (HPLC)
$^c$w/w % from quantitative analytical method 2 (GC)
$^d$calculated from purity and content of the three known impurities shown in this table
$^e$not detected Quantitative Analytical Method 1 (HPLC):

Agilent device with Agilent Zorbax Eclipse XDB-C18, 1.4 mL/min acetonitrile/water with 0.1 vol % phosphoric acid, UV detection at 210 nm.

Quantitative Analytical Method 2 (GC):

Agilent 6890N with Agilent CP7667, 3 mL/min H2, injection at 280° C., 8 min at 60° C., with 15° C./min to 280° C., detection (FID) at 320° C.

The invention claimed is:

1. A process for the preparation of the ketone compounds of formula (II)

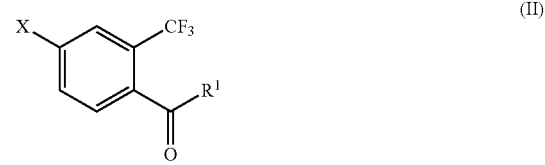

wherein
X is F or Cl and
$R^1$ is $C_1$-$C_6$-alkyl or $C_3$-$C_8$-cycloalkyl;
comprising the following step:
(i) reacting a compound of the formula (III)

with R'—Mg-Hal (IV) or Mg, and $R^1C(=O)Cl$ (V),
wherein the Grignard reagent is added as solution in a solvent selected from tetrahydrofurane (THF), 1,4-dioxane, diethylether and 2-methyl-tetrahydrofurane,
wherein the temperature during the reaction with (V) is kept in the range of −20° C. to 10° C.,
wherein
$R^1$ is $C_1$-$C_4$-alkyl or $C_3$-$C_6$-cycloalkyl and
Hal is halogen.

2. The process of claim 1, wherein a Cu(I)-catalyst is added in step (i).

3. The process of claim 2, wherein the Cu(I)-catalyst is Cu(I)Cl.

4. The process of claim 1, wherein R' is iso-propyl.

5. The process of claim 1, wherein Hal is Br or Cl, in particular Br.

6. The process of claim 1, wherein X is F.

7. The process of claim 1, wherein $R^1$ is selected from $CH_3$, $CH(CH_3)_2$ and cyclopropyl.

8. The process of claim 1, wherein the temperature during the reaction with (V) is kept in the range of −15° C. to 5° C.

9. The process of claim 1, wherein the temperature during the reaction with (V) is kept in the range of −10° C. to −5° C.

10. A process for the preparation of triazole compounds of the formula (IC)

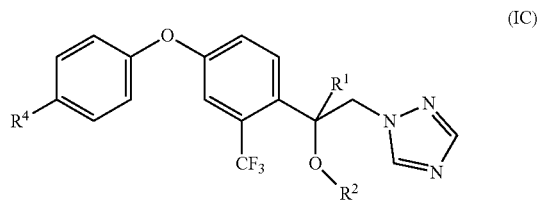

wherein $R^1$ is $C_1$-$C_6$-alkyl or $C_3$-$C_8$-cycloalkyl; and
$R^2$ is hydrogen, $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkyl-$C_1$-$C_6$-alkyl, phenyl, phenyl-$C_1$-$C_4$-alkyl, phenyl-$C_2$-$C_4$-alkenyl or phenyl-$C_2$-$C_4$-alkynyl;
  wherein the aliphatic moieties of $R^2$ are not further substituted or do carry one, two, three or up to the maximum possible number of identical or different groups
  $R^{12a}$ which independently are selected from:
  $R^{12a}$ halogen, OH, CN, nitro, $C_1$-$C_4$-alkoxy, $C_3$-$C_8$-cycloalkyl, $C_3$-$C_8$-halocycloalkyl and $C_1$-$C_4$-halogenalkoxy;
  wherein the cycloalkyl and/or phenyl moieties of $R^2$ are not further substituted or do carry one, two, three, four, five or up to the maximum number of identical or different groups $R^{12b}$ which independently are selected from:
  $R^{12b}$ halogen, OH, CN, nitro, $C_1$-$C_4$-alkyl, $C_1$-$C_4$-alkoxy, $C_1$-$C_4$-halogenalkyl, $C_3$-$C_8$-cycloalkyl, $C_3$-$C_8$-halocycloalkyl and $C_1$-$C_4$-halogenalkoxy; and
$R^4$ is F or Cl
comprising the following steps:
(i) preparing a compound of formula (II)

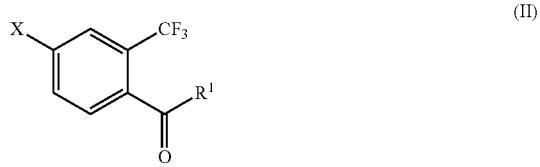

by reacting a compound of the formula (III)

with R'—Mg-Hal (IV) or Mg, and $R^1C(=O)Cl$ (V),
wherein the Grignard reagent is added as solution in a solvent selected from tetrahydrofurane (THF), 1,4-dioxane, diethylether and 2-methyl-tetrahydrofurane,
wherein the temperature during the reaction with (V) is kept in the range of −20° C. to 10° C.,
wherein
R' is $C_1$-$C_4$-alkyl or $C_3$-$C_6$-cycloalkyl and
Hal is halogen;
(ii) reacting compound (II) as defined in step (i) with a phenol derivative of formula (VI)

wherein
R" is hydrogen or an alkali metal kation;
in the presence of a base if R" is hydrogen to result in a ketone of formula (IA)

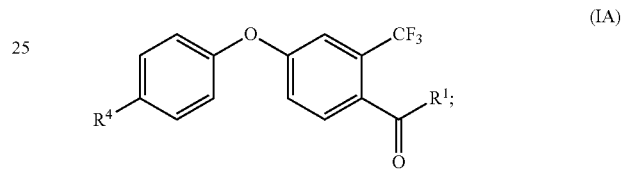

(iii) reacting the ketone of the formula (IA) as defined in step (ii) to oxiranes (IB);

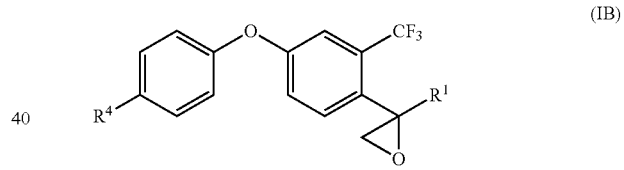

and
(iv) reacting the oxirane (IB) as defined in step (iii) with 1H-1,2,4-triazole in the presence of a base to obtain compounds (IC), wherein $R^2$ is hydrogen (compounds IC-1);
  and, for obtaining compounds wherein $R^2$ is different from hydrogen (compounds IC-2);
(v) derivatizing the compound of formula (IC-1) as defined in step (iv) under basic conditions with $R^2$-LG, wherein LG is a nucleophilically replaceable leaving group; to result in compounds (IC-2).

11. The process of claim 10, wherein the reaction to the oxirane (IB) is carried out with a trimethylsulf(ox)onium halide (($CH_3)_3S^+$ (O)Hal$^-$) (VII), wherein Hal is halogen, or trimethylsulfonium methylsulfate of the formula (VIII) ($CH_3)_3S^+$ $CH_3SO_4^-$.

12. The process of claim 10, wherein $R^4$ is Cl.

* * * * *